United States Patent [19] [11] Patent Number: 5,989,285
DeVilbiss et al. [45] Date of Patent: Nov. 23, 1999

[54] TEMPERATURE CONTROLLED BLANKETS AND BEDDING ASSEMBLIES

[75] Inventors: Roger S. DeVilbiss, Dallas; Tony M. Quisenberry, Highland Village; Sathya Rajasubramanian, Arlington, all of Tex.

[73] Assignee: Thermotek, Inc., Carrollton, Tex.

[21] Appl. No.: 08/695,980

[22] Filed: Aug. 15, 1996

[51] Int. Cl.[6] ................................................. A61F 7/00
[52] U.S. Cl. .......................................... 607/107; 607/104
[58] Field of Search ................................... 607/104, 107, 607/108, 112; 165/46; 5/482, 485

[56] References Cited

U.S. PATENT DOCUMENTS

| | | |
|---|---|---|
| 773,828 | 11/1904 | Titus et al. . |
| 2,110,022 | 3/1938 | Kliesrath ................................. 607/104 |
| 2,504,308 | 4/1950 | Donkle, Jr. ................................. 62/129 |
| 3,014,117 | 12/1961 | Madding ................................. 219/46 |
| 3,345,641 | 10/1967 | Jennings ................................. 21/2.1 |
| 3,367,319 | 2/1968 | Carter, Jr. ................................. 126/204 |
| 3,608,091 | 9/1971 | Olson et al. ................................. 2/2.1 |
| 3,660,849 | 5/1972 | Jonnes et al. ................................. 2/2.1 |
| 3,736,764 | 6/1973 | Chambers et al. ............................ 62/89 |
| 3,738,702 | 6/1973 | Jacobs ................................. 297/180 |
| 3,744,053 | 7/1973 | Parker et al. ................................. 2/2.1 |
| 3,894,213 | 7/1975 | Agarwala ................................. 219/297 |
| 4,006,604 | 2/1977 | Seff ................................. 62/261 |
| 4,459,822 | 7/1984 | Pasternack ............................ 62/259.3 |
| 4,547,906 | 10/1985 | Nishida et al. ................................. 2/93 |
| 4,660,388 | 4/1987 | Greene, Jr. ................................. 62/261 |
| 4,821,354 | 4/1989 | Little ................................. 5/422 |
| 4,884,304 | 12/1989 | Elkins ................................. 5/421 |
| 4,962,761 | 10/1990 | Golden ................................. 607/104 |
| 4,979,375 | 12/1990 | Nathans et al. ........................ 62/259.3 |
| 4,996,970 | 3/1991 | Legare ................................. 126/205 |
| 5,044,364 | 9/1991 | Crowther ................................. 607/107 |
| 5,092,271 | 3/1992 | Kleinsasser ................................. 119/20 |
| 5,097,829 | 3/1992 | Quisenberry ............................ 128/400 |
| 5,106,373 | 4/1992 | Augustine et al. ..................... 604/113 |
| 5,125,238 | 6/1992 | Ragain et al. ........................ 62/259.3 |
| 5,165,127 | 11/1992 | Nicholson ................................. 5/421 |
| 5,184,612 | 2/1993 | Augustine ................................. 128/400 |
| 5,243,706 | 9/1993 | Frim et al. ................................. 2/2 |
| 5,300,101 | 4/1994 | Augustine et al. ..................... 607/107 |
| 5,300,102 | 4/1994 | Augustine et al. ..................... 607/107 |
| 5,300,103 | 4/1994 | Stempel et al. ........................ 607/108 |
| 5,324,320 | 6/1994 | Augustine et al. ..................... 607/107 |
| 5,336,250 | 8/1994 | Augustine ................................. 607/107 |
| 5,343,579 | 9/1994 | Dickerhoff et al. ........................ 5/421 |
| 5,350,417 | 9/1994 | Augustine ................................. 607/104 |
| 5,354,117 | 10/1994 | Danielson et al. ................. 297/180.15 |
| 5,360,439 | 11/1994 | Dickerhoff et al. ................... 607/104 |
| 5,371,665 | 12/1994 | Quisenberry et al. .................... 363/89 |
| 5,402,542 | 4/1995 | Viard ................................. 5/421 |
| 5,405,370 | 4/1995 | Irani ................................. 607/104 |
| 5,405,371 | 4/1995 | Augustine et al. ..................... 607/107 |
| 5,411,494 | 5/1995 | Rodriguez ................................. 604/290 |
| 5,411,541 | 5/1995 | Bell et al. ................................. 607/104 |
| 5,528,485 | 6/1996 | DeVilbiss et al. ........................ 363/89 |
| 5,561,981 | 10/1996 | Quisenberry et al. .................... 62/3.7 |
| 5,566,062 | 10/1996 | Quisenberry et al. .................... 363/89 |

FOREIGN PATENT DOCUMENTS 689674 10/1979 Russian Federation ............... 607/104

*Primary Examiner*—Mark S. Graham
*Attorney, Agent, or Firm*—Jenkens & Gilchrist, P.C.

[57] ABSTRACT

A temperature controlled blanket and a temperature controlled bedding system have provision of both recirculating temperature controlled fluid and temperature controlled gas to enhance performance for convectively heating or cooling a patient. Counter flow or co-flow heat exchanging principles between the temperature controlled liquid and the temperature controlled gas achieves temperature uniformity across different sections of the blanket and the bedding system. Drapes in the temperature controlled bedding system provide a gas envelope around a person using the bedding system. In a further embodiment of the bedding system, the air portion of the bedding system is provided for use with a patient bed which supplies the fluid portion of the overall bedding system. In a further embodiment of the bedding system, the fluid portion of the bedding system is provided for use with a patient bed which supplies the air portion of the overall bedding system.

40 Claims, 9 Drawing Sheets

TEMPERATURE CONTROLLED BLANKETS AND BEDDING ASSEMBLIES

BACKGROUND OF THE INVENTION

1. Field of the Invention

The present invention relates to temperature controlled blankets and temperature controlled bedding assemblies, and more particularly, but not by way of limitation, to temperature controlled blankets and temperature controlled bedding assemblies to be operatively positioned with respect to a person for selective heating or cooling that person using a temperature controlled forced-gas convection system or a temperature controlled fluid recirculating system or a combination of both systems to enhance performance of the blankets and bedding systems.

2. History of the Prior Art

Medical care providers have long recognized the need to provide warmth and cooling directly to patients as part of their treatment and therapy. Better recoveries have been reported using cold therapy for orthopaedic patients. The benefits of warming patients undergoing surgery has been conclusively proven.

Several devices have been developed that deliver temperature controlled fluids through pads or convective thermal blankets to achieve the above purpose. Typically these devices have a heating or a cooling element, a source for the fluid, a pump for forcing the fluid through the pad or blanket and a thermal interface between the patient and the temperature controlled fluid. U.S. Pat. No. 4,884,304 to Elkins is directed to a mattress cover device which contains liquid flow channels which provide the selective heating or cooling by conduction.

Devices have also been developed for providing heat to a person in bed. Electric blankets containing electric heating elements have been used for years to warm a person in bed.

Cooling blankets have also been proposed such as the blanket disclosed in U.S. Pat. No. 4,660,388 to Greene. Greene discloses a cooling cover having an inflatable pad with plenum chambers at opposite ends thereof. Cool air is generated in a separate unit and directed to the pad and out a number of apertures on the underside of the pad and against the body of the person using the cover.

A disposable heating or cooling blanket is disclosed in U.S. Pat. No. 5,125,238 to Ragan, et al which has three layers of flexible sheeting. Two of the layers form an air chamber and the third includes a comfortable layer for contact with the patient. Conditioned air is directed toward the covered person through a multiplicity of orifices in the bottom layers of the blanket.

Several problems are inherent in the prior art devices. The prior art devices lack uniform temperature control. The temperature of the blankets closest to the machine supplying the conditioned air to the blanket is warmer or cooler than the remaining parts of the blanket depending upon whether the blanket is providing heating or cooling to the patient.

The present invention provides an improvement over the prior art blankets and bedding systems by providing an efficient uniform temperature controlled gaseous fluid for convectively heating or cooling the patient by using a liquid fluid with a significantly larger thermal capacity to uniformly heat or cool the gaseous fluid delivered to the patient. A further significant advantage of the present invention is the use of counter flow or co-flow heat exchanging principles to achieve temperature uniformity across different sections of the blanket.

SUMMARY OF THE INVENTION

One aspect of the present invention comprises a temperature controlled blanket with both recirculating temperature controlled fluid and temperature controlled gas to enhance performance for convectively heating or cooling a patient covered by the temperature controlled blanket.

Another aspect of the present invention comprises a top and middle sheet secured to each other to form first and second distribution chambers located at opposite ends of a first plurality of separate passages for the flow of a temperature controlled liquid therethrough. A bottom sheet is removably attached to the middle sheet to form third and fourth distribution chambers located at opposite ends of a second plurality of separate passages for the flow of a temperature controlled gas therethrough. A plurality of apertures are formed in the second plurality of separate passages to allow the temperature controlled gas to escape toward the patient. The second plurality of separate passages are in alignment with the first plurality of separate passages. Counter flow or co-flow heat exchanging principles between the temperature controlled liquid and the temperature controlled gas achieves temperature uniformity across different sections of the blanket.

In another aspect, the above described present invention includes a soft fabric material secured to the surface of the top sheet which is to be farthest from the patient.

In yet another aspect, the above described present invention includes a sheet of insulating material secured to the surface of the top sheet which is to be farthest from the patient.

In yet another aspect, the above described present invention includes a heating/cooling system connected to the temperature controlled blanket or bedding system for selectively circulating temperature controlled liquid either in counter flow or co-flow with the circulating temperature controlled gas.

In yet another aspect, the present invention comprises a top and middle sheet secured to each other to form first and second distribution chambers located at opposite ends of a plurality of separate passages for the flow of a temperature controlled liquid therethrough. A bottom sheet is removably attached to the middle sheet to form a gas chamber which covers the first and second distribution chambers and the plurality of separate passages for the flow of a temperature controlled gas through the gas chamber. A plurality of apertures are formed in the bottom sheet to allow the temperature controlled gas to escape toward the patient.

In yet another aspect, the present invention comprises a temperature controlled bedding system with both recirculating temperature controlled fluid and temperature controlled gas to enhance performance for convectively heating or cooling a patient laying on the temperature controlled bedding system.

In yet another aspect, the above temperature controlled bedding system includes drapes to close around the patient and provide a gas envelope around the patient.

In yet another aspect, the temperature controlled bedding system comprises an air portion of the bedding system which can be used with a patient bed which supplies the fluid portion of the overall bedding system.

In yet another aspect, the temperature controlled bedding system comprises a fluid portion of the bedding system which can be used with a patient bed which supplies the air portion of the overall bedding system.

BRIEF DESCRIPTION OF THE DRAWINGS

Other advantages and features of the invention will become more apparent with reference to the following detailed description of a presently preferred embodiment thereof in connection with the accompanying drawings, wherein like reference numerals have been applied to like elements, in which.

DETAILED DESCRIPTION

Figure 1:
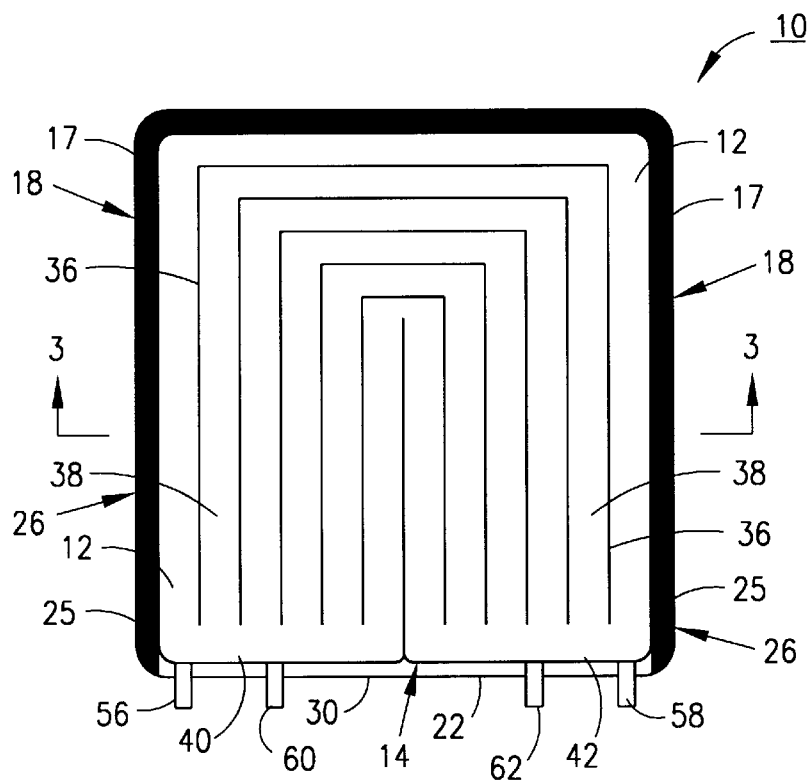
FIG. 1 is a view of the top surface of the temperature controlled blanket according to the present invention.
Figure 2:
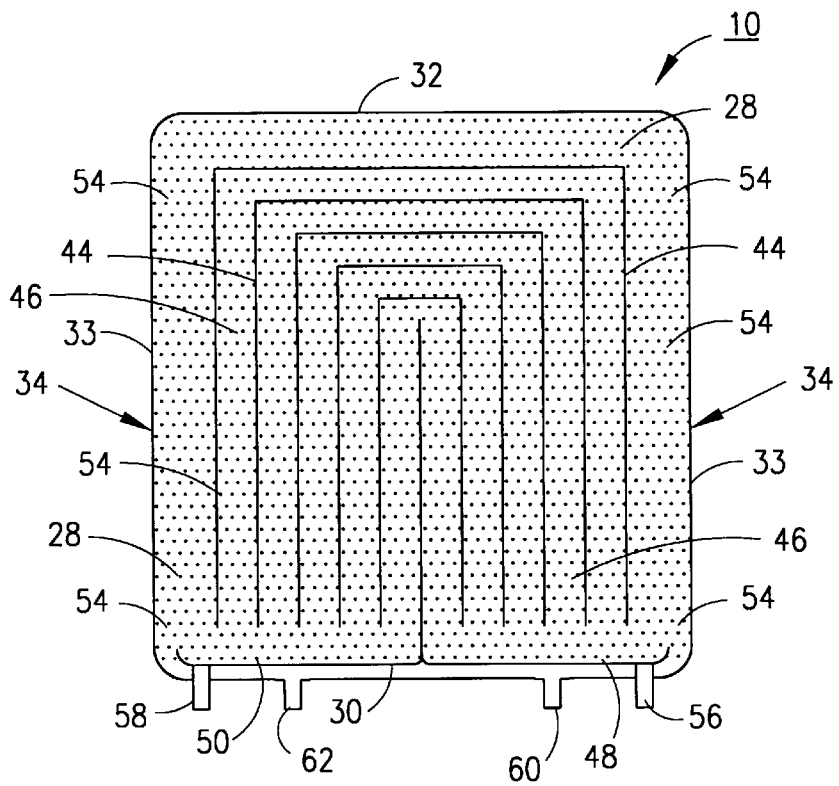
FIG. 2 is a view of the bottom surface of the temperature controlled blanket shown in FIG. 1.
Figure 3:
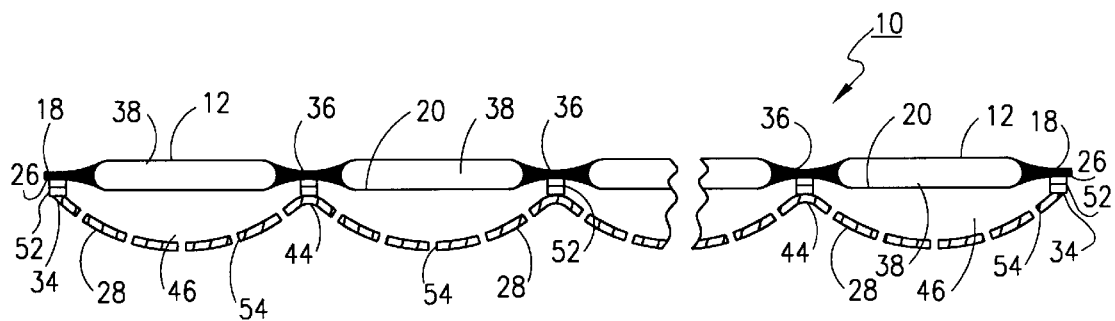
FIG. 3 is an enlarged sectional view of the present invention taken along line 3—3 in FIG. 1.

Referring now to the drawings, and in particular to FIGS. 1–3, a temperature controlled blanket according to the present invention is referred to generally by reference numeral 10. Temperature controlled blanket 10, of this particular embodiment, comprises a top sheet 12 having a first end 14, an opposing second end 16 and side edges 17 to form a periphery 18; a middle sheet 20 having a first end 22, an opposing second end 24 and side edges 25 to form a periphery 26 and a bottom sheet 28 having a first end 30, an opposing second end 32 and side edges 33 to form a periphery 34. The orientation of the sheets of material comprising the temperature controlled blanket 10 is with respect to the person or patient covered by the blanket with the bottom sheet being next to the person or patient being covered with the temperature controlled blanket.

The temperature controlled blanket 10 is typically used to adjust or maintain the patients body temperature through the application of either warming or cooling gas, e.g. air, for surgical, post operative, hypothermic or hyperthermic patients.

Top sheet 12 and middle sheet 20 are formed of a fluid impermeable heat bondable plastic such as polyethylene, polyvinylchloride, or other similar material. Top sheet 12 is attached or secured to middle sheet 20 along their periphery 18 and 26, respectively, and along a first plurality of parallel portions 36 by RF (radio frequency) bonding or heat bonding to form a first plurality of separate passages 38 therebetween and to form a first distribution chamber 40 and a second distribution chamber 42 which are located at opposite ends of the first plurality of separate passages 38 and in fluid communication therewith. The first plurality of separate passages 38 are formed in the shape of a U from the first distribution chamber 40 to the second distribution chamber 42.

Bottom sheet 28 is formed of a flexible material such as a fabric material. In the preferred embodiment, the fabric material comprises linen. Bottom sheet 28 is removably attached to middle sheet 20 along their periphery 34 and 26, respectively, and along a second plurality of parallel portions 44 to form a second plurality of separate passages 46 therebetween and to form a third distribution chamber 48 and a fourth distribution chamber 50 which are located at opposite ends of the second plurality of separate passages 46. The second plurality of separate passages 46 are formed in the shape of a U from the third distribution chamber 48 to the fourth distribution chamber 50.

Bottom sheet 28 is removably attached to middle sheet 20 along their periphery 34 and 26, respectively, and along the second plurality of parallel portions 44 by fastening means 52 such as VELCRO with one-half of the velcro being attached, by conventional means, to the bottom sheet 28 and the other half of the VELCRO being attached, by conventional means, to the middle sheet 20. The second plurality of parallel portions 44 are in alignment with the first plurality of parallel portions 36. A plurality of apertures 54 are formed in bottom sheet 28 along the surface of the second plurality of separate passages 46 to allow temperature controlled gas within the second plurality of separate passages 46 to escape toward and against the person covered by the temperature controlled blanket 10. The number and size of the apertures 54 are commensurate with the specifications of the heating/cooling system (to be discussed below) which supplies the temperature controlled gas to either the third distribution chamber 48 or the fourth distribution chamber 50 and then on to the second plurality of separate passages 46.

It will be appreciated that for purposes of sanitation, the removable bottom sheet 28 is disposed of after the use thereof and is not used again.

A first port 56 is in fluid communication with first distribution chamber 40 to either receive temperature controlled liquid, e.g. water, from or discharge temperature controlled liquid to the heating/cooling system to be used with the temperature controlled blanket 10. First port 56 is provided in either the top sheet 12 or the middle sheet 20.

A second port 58 is in fluid communication with second distribution chamber 42 to either receive temperature controlled liquid from or discharge temperature controlled liquid to the heating/cooling system to be used with the temperature controlled blanket 10. Second port 58 is provided in either the top sheet 12 or the middle sheet 20. It will be appreciated that when first port 56 is receiving temperature controlled liquid then second port 58 will be discharging temperature controlled liquid and vice versa.

A third port 60 is in fluid communication with third distribution chamber 48 to either receive temperature controlled gas, e.g. air, from or discharge temperature controlled gas to the heating/cooling system to be used with the temperature controlled blanket 10. Third port 60 is attached by conventional means to the surface of middle sheet 20 which faces the bottom sheet 28.

A fourth port 62 is in fluid communication with fourth distribution chamber 50 to either receive temperature controlled gas from or discharge temperature controlled gas to the heating/cooling system to be used with the temperature controlled blanket 10. Fourth port 62 is attached by conventional means to the surface of middle sheet 20 which faces the bottom sheet 28. It will be appreciated that when third port 60 is receiving temperature controlled gas then fourth port 62 will be discharging temperature controlled gas and vice versa.

Figure 4:
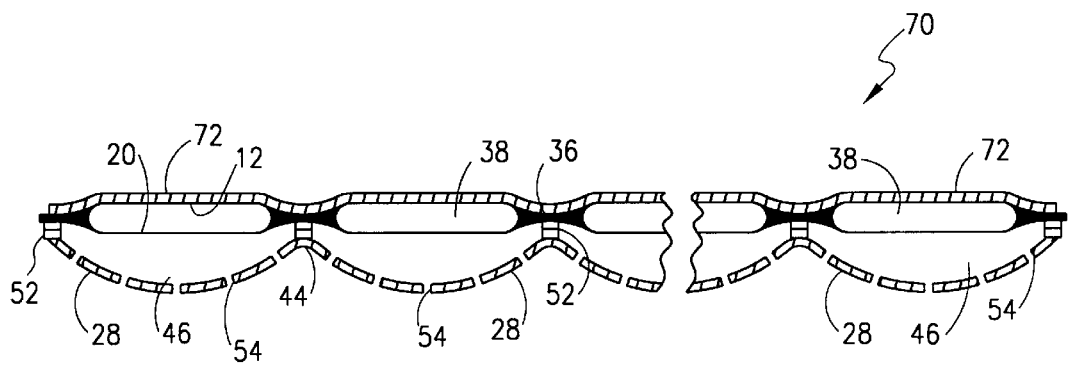
FIG. 4 is an enlarged sectional view similar to that of FIG. 3 showing an additional embodiment of the present invention.

Referring now to FIG. 4, the reference numeral 70 generally indicates an additional embodiment of the present invention. Temperature controlled blanket 70 is similar to temperature controlled blanket 10 in that it includes all the elements of temperature controlled blanket 10 and further includes sheet 72 which is secured to the surface of top sheet 12 which is furthermost from the person covered with the blanket. Sheet 72 comprises a soft fabric material which is attached to top sheet 12 by conventional means such as RF bonding, heat bonding, adhesives, etc.

Figure 5:
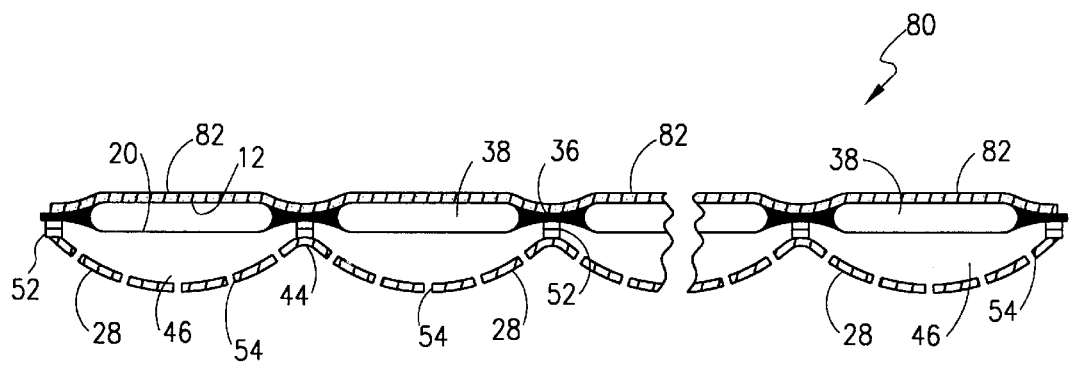
FIG. 5 is an enlarged sectional view similar to that of FIG. 3 showing another additional embodiment of the present invention.

Referring now to FIG. 5, the reference numeral 80 generally indicates an additional embodiment of the present invention. Temperature controlled blanket 80 is similar to temperature controlled blanket 10 in that it includes all the elements of temperature controlled blanket 10 and further includes sheet 82 which is secured to the surface of top sheet 12 which is furthermost from the person covered with the blanket. Sheet 82 comprises an insulating material which is attached to top sheet 12 by conventional means such as RF bonding, heat bonding, adhesives, etc. It will be appreciated that the purpose of sheet 82 is to assist in retaining heat or cold in the temperature controlled liquid maintained in first distribution chamber 40, second distribution chamber 42 and the first plurality of separate passages 38 and reduce the loss of heat or cold to the ambient.

Figure 6:
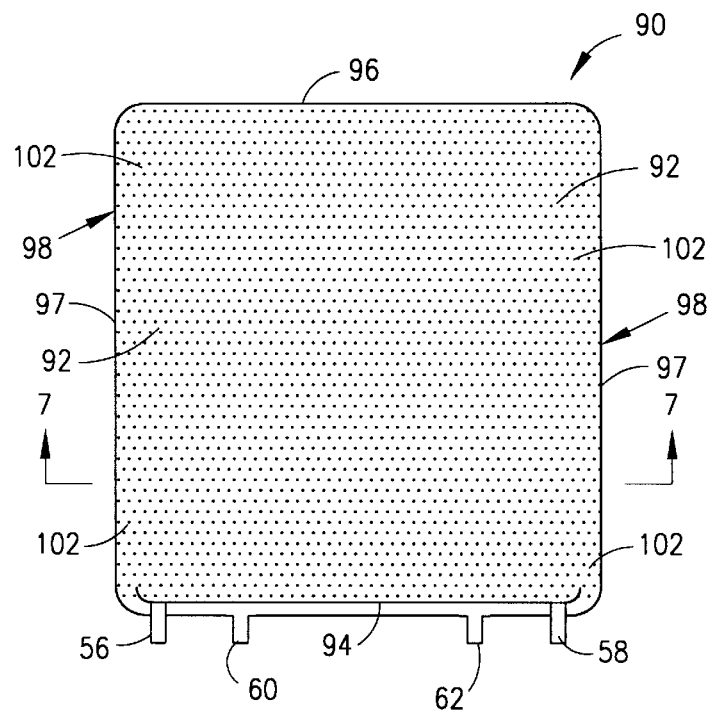
FIG. 6 is a view of the bottom surface of an additional embodiment of the present invention.
Figure 7:
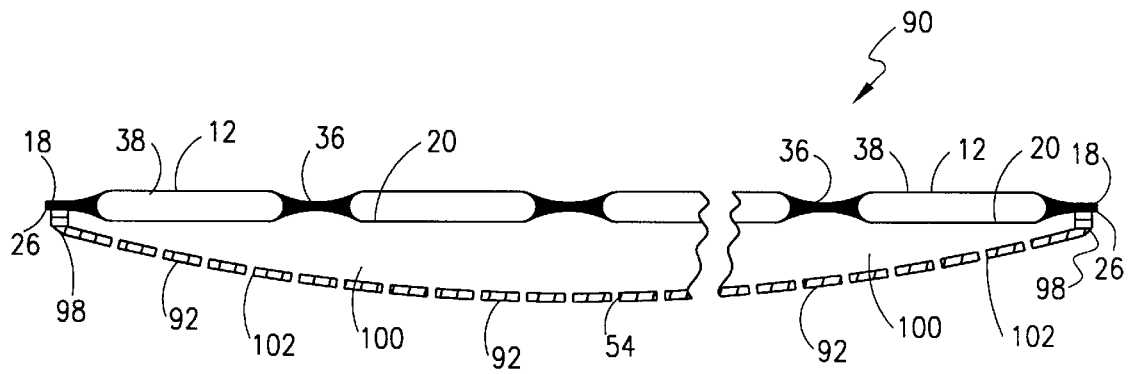
FIG. 7 is an enlarged sectional view of the additional embodiment of the present invention taken along line 7—7 in FIG. 6.

Referring now to FIGS. 6 and 7, the reference numeral 90 generally indicates an additional embodiment of the present invention. Temperature controlled blanket 90, of this particular embodiment, comprises a top sheet 12 having a first end 14, an opposing second end 16 and side edges 17 to form a periphery 18 (see FIG. 1); a middle sheet 20 having a first end 22, an opposing second end 24 and side edges 25 to form a periphery 26 (see FIG. 1) and a bottom sheet 92 having a first end 94 (in alignment with first end 22), an opposing second end 96 (in alignment with opposing second end 24) and side edges 97 to form a periphery 98. The orientation of the sheets comprising the temperature controlled blanket 90 is with respect to the person or patient covered by the blanket with the bottom sheet being next to the person or patient being covered with the temperature controlled blanket.

Bottom sheet 92 is formed of a flexible material such as a fabric material. In the preferred embodiment, the fabric material comprises linen. Bottom sheet 92 is removably attached to middle sheet 20 along their periphery 98 and 26, respectively, to form a gas chamber 100. A plurality of apertures 102 are formed in bottom sheet 92 to allow temperature controlled gas within gas chamber 100 to escape toward and against the person covered by the temperature controlled blanket 90. The number and size of the apertures 102 are commensurate with the specifications of the heating/cooling system (to be discussed below) which supplies the temperature controlled gas to gas chamber 100.

Figure 8:
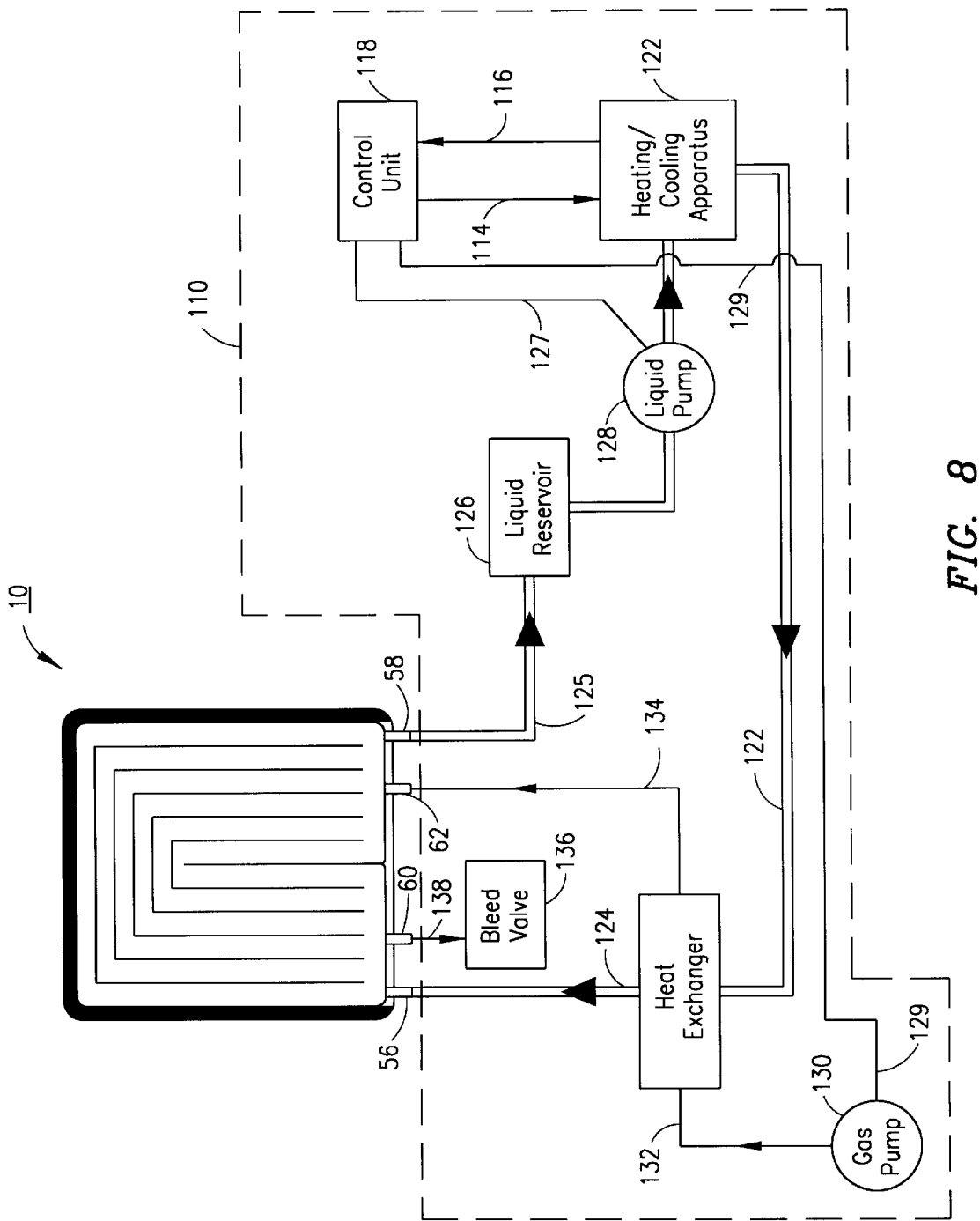
FIG. 8 is a schematic view showing the heating/cooling system operatively connected to the inventive temperature controlled blanket.

Referring now to FIG. 8, the reference numeral 110 generally indicates a heating/cooling system for supplying temperature controlled liquid, e.g. water, and temperature controlled gas, e.g. air, to the temperature controlled blanket 10. Heating/cooling system 110 comprises heating/cooling apparatus 112 connected by cables 114 and 116 to control unit or circuitry 118 and connected in fluid communication with heat exchanger 120 by conduit, pipe or tubing 122. Heat exchanger 120 is connected in fluid communication to first port 56 in temperature controlled blanket 10 by conduit, pipe or tubing 124. Second port 58 is connected in fluid communication with liquid reservoir 126 by conduit, pipe or tubing 125. Liquid reservoir 126 is connected in liquid communication with heating/cooling apparatus 112 through liquid pump 128. Gas pump 130 is connected in fluid communication with heat exchanger 120 by conduit, pipe or tubing 132 and heat exchanger 120 is connected in fluid communication with fourth port 62 in temperature controlled blanket 10 by conduit, pipe or tubing 134. Third port 60 is connected in fluid communication with gas bleed valve 136 by conduit, pipe or tubing 138. Gas bleed valve 136 provides means to control the pressure of the temperature controlled gas in the temperature controlled blanket 10.

In operation, the person operating the system turns the system on, chooses heat or cold and inputs the desired temperature via the input controls on control unit 118. Control signals from control unit 118 are input to heating/cooling apparatus 112 via cable 114, to liquid pump 128 via cable 127 and to gas pump 130 via cable 129. Temperature feedback from heating/cooling apparatus 112 is transmitted to control unit 118 over cable 116.

Temperature controlled liquid flows from the heating/cooling unit 112 through heat exchanger 120 to first port 56, on to first distribution chamber 40, through first plurality of separate passages 38 to second distribution chamber 42 and then out second port 58 to liquid reservoir 126, on to liquid pump 128 and then returns to heating/cooling apparatus 112.

Temperature controlled gas flows from gas pump 130 through heat exchanger 120 to fourth port 62, on to fourth distribution chamber 50, through second plurality of separate passages 46 to third distribution chamber 48 and then out third port 60 to gas bleed valve 136.

It will be appreciated that the flow of temperature controlled liquid and the flow of temperature controlled gas are in the same direction or co-flow through the temperature controlled blanket 10. It will also be appreciated that if conduits, pipes or tubes 124 and 125 are changed such that conduit, pipe or tubing 124 is connected to second port 58 and conduit, pipe or tubing 125 is connected to first port 56, then the flow of temperature controlled liquid will be opposite or counter flow to the flow of the temperature controlled gas through the temperature controlled blanket 10.

Figure 9:
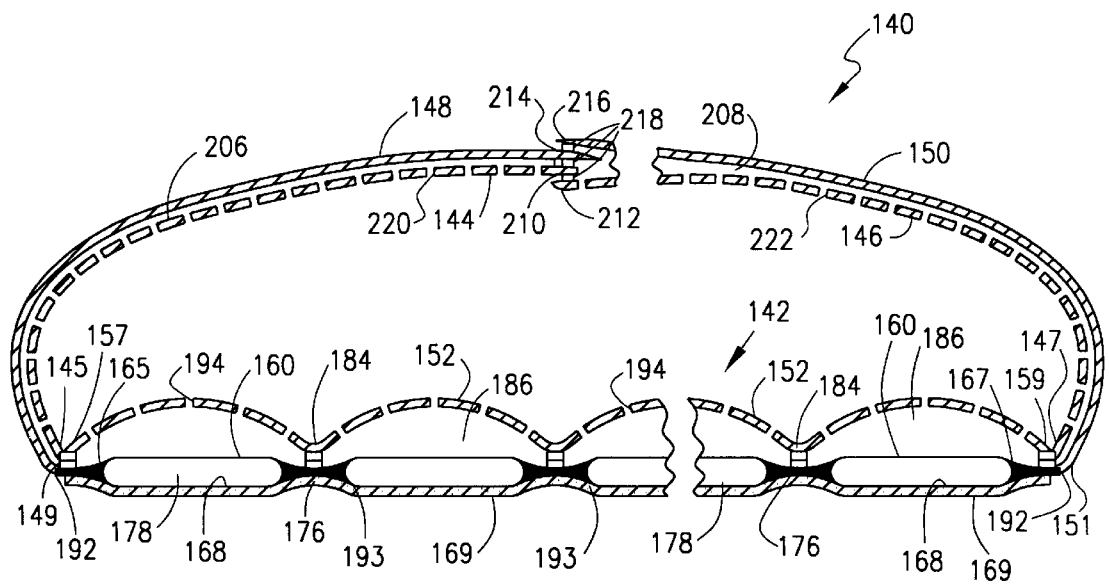
FIG. 9 is an enlarged sectional view similar to that of FIG. 5 showing an additional embodiment of the present invention.

Referring now to FIG. 9, the reference numeral 140 generally indicates an additional embodiment of the present invention in the form of a bedding system. Bedding system 140 is typically used to adjust or maintain the patients body temperature through the application of either warming or cooling gas, e.g. air, for surgical, post operative, hypothermic or hyperthermic patients.

It will be appreciated that bedding system 140, as disclosed in FIG. 9, comprises the elements of temperature controlled blanket 80 to form the central portion 142 of bedding system 140 and drapes are added which enclose the patient or person. Bedding system 140 is positioned on a bed and the patient is positioned on the central portion 142 and the drapes are then positioned over the patient to provide a gas envelope around the patient. The orientation of the sheets of material comprising the central portion 142 of the bedding system 140 is with respect to the patient or person laying on the central portion 142 with the top sheet being next to the patient or person laying on the central portion 142.

Figure 10:
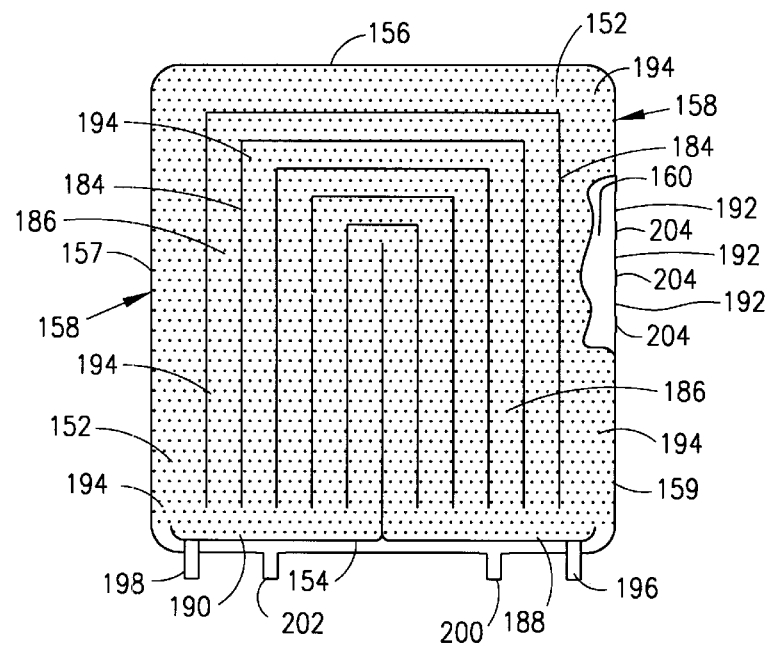
FIG. 10 is a view of the top surface of the central portion of the bedding system of FIG. 9 without the drapes to show the passageways allowing inflation of the drapes.
Figure 11:
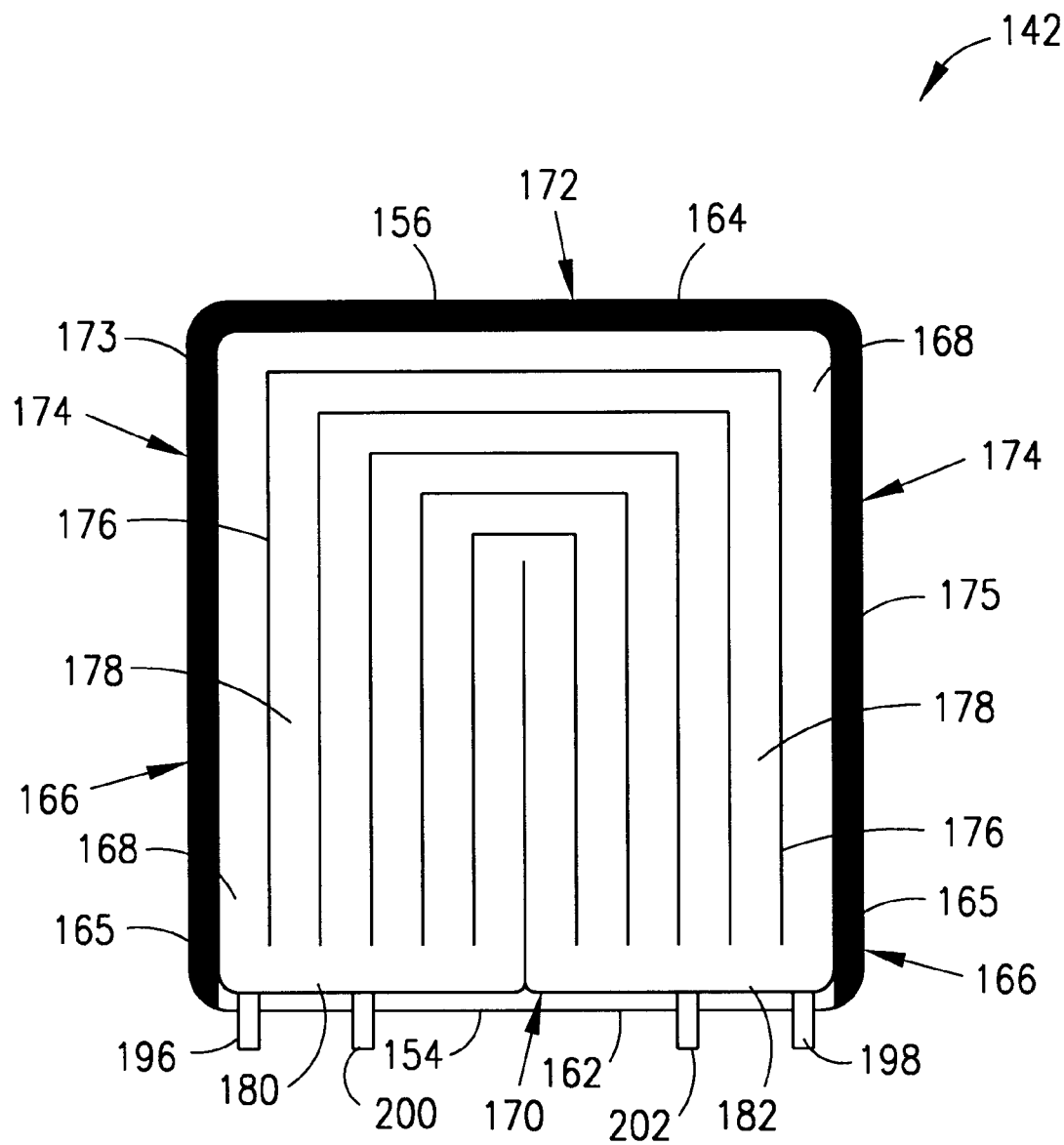
FIG. 11 is a view of the bottom surface of the central portion of the bedding system of FIG. 9.

Referring now to FIGS. 9–11, bedding system 140 comprises central portion 142 and drapes 144, 146, 148 and 150. Central portion 142 comprises a top sheet 152 having a first end 154, an opposing second end 156, a first side edge 157 and a second opposing side edge 159 to form a periphery 158; a middle sheet 160 having a first end 162, an opposing second end 164, a first side edge 165 and a second opposing side edge 167 to form a periphery 166 and a bottom sheet 168 having a first end 170, an opposing second end 172, a first side edge 173 and a second opposing side edge 175 to form a periphery 174.

Bottom sheet 168 and middle sheet 160 are formed of a fluid impermeable heat bondable plastic such as polyethylene, polyvinylchloride, or other similar material. Bottom sheet 168 is attached or secured to middle sheet 160 along their periphery 174 and 166, respectively, and along a first plurality of parallel portions 176 by RF (radio frequency) bonding or heat bonding to form a first plurality of separate passages 178 therebetween and to form a first distribution chamber 180 and a second distribution chamber 182 which are located at opposite ends of the first plurality of separate passages 178 and in fluid communication therewith. The first plurality of separate passages 178 are formed in the shape of a U from the first distribution chamber 180 to the second distribution chamber 182. Sheet 169 may be included as part of central portion 142 by securing sheet 169 to the surface of bottom sheet 168 which is furthermost from the person laying on central portion 142. Sheet 169 comprises an insulating material which is attached to bottom sheet 168 by conventional means such as RF bonding, heat bonding, adhesives, etc. It will be appreciated that the purpose of sheet 169 is to assist in retaining heat or cold in the temperature controlled liquid maintained in first distribution chamber 180, second distribution chamber 182 and the first plurality of separate passages 178 and reduce the loss of heat or cold to the ambient.

Top sheet 152 is formed of a flexible material such as a fabric material. In the preferred embodiment, the fabric material comprises linen. Top sheet 152 is removably attached to middle sheet 160 along their periphery 158 and 166, respectively, and along a second plurality of parallel portions 184 to form a second plurality of separate passages 186 therebetween and to form a third distribution chamber 188 and a fourth distribution chamber 190 which are located at opposite ends of the second plurality of separate passages 186. The second plurality of separate passages 186 are formed in the shape of a U from the third distribution chamber 188 to the fourth distribution chamber 190.

Drape 144 includes a first side edge 145, a second opposing side edge 210 and a length at least as long as the length of top sheet 152. Drape 146 includes a first side edge 147, a second opposing side edge 212 and a length at least as long as the length of top sheet 152. Drape 148 includes a first side edge 149, a second opposing side edge 214 and a length at least as long as the length of top sheet 152. Drape 150 includes a first side edge 151, a second opposing side edge 216 and a length at least as long as the length of top sheet 152.

Top sheet 152, drape 144, drape 148 and middle sheet 160 are removably attached together along their first side edges 157, 145, 149 and 165, respectively, by fastening means 192 such as VELCRO. First side edge 147 of drape 146, first side edge 151 of drape 150, second opposing side edge 159 of top sheet 152 and the second opposing side edge 167 of middle sheet 160 are removably attached together by fastening means 192 such as VELCRO. Top sheet 152 is also removably attached to middle sheet 160 along their peripheries 158 and 166, respectively, and along the second plurality of parallel portions 184 by fastening means 193 such as VELCRO. The second plurality of parallel portions 184 are in alignment with the first plurality of parallel portions 176. A plurality of apertures 194 are formed in top sheet 152 along the surface of the second plurality of separate passages 186 to allow temperature controlled gas within the second plurality of separate passages 186 to escape toward and against the person laying on the central portion 142 of bedding system 140. The number and size of the apertures 194 are commensurate with the specifications of the heating/cooling system 110 (which was previously discussed) which supplies the temperature controlled gas to either the third distribution chamber 188 or the fourth distribution chamber 190 and then on to the second plurality of separate passages 186.

It will be appreciated that for purposes of sanitation, the removable top sheet 152 is disposed of after the use thereof and is not used again.

A first port 196 is in fluid communication with first distribution chamber 180 to either receive temperature controlled liquid, e.g. water, from or discharge temperature controlled liquid to the heating/cooling system 110 to be used with the bedding system 140. First port 196 is provided in either the bottom sheet 168 or the middle sheet 160.

A second port 198 is in fluid communication with second distribution chamber 182 to either receive temperature controlled liquid from or discharge temperature controlled liquid to the heating/cooling system 110 to be used with the bedding system 140. Second port 198 is provided in either the bottom sheet 168 or the middle sheet 160. It will be appreciated that when first port 196 is receiving temperature controlled liquid then second port 198 will be discharging temperature controlled liquid and vice versa.

A third port 200 is in fluid communication with third distribution chamber 188 to either receive temperature controlled gas, e.g. air, from or discharge temperature controlled gas to the heating/cooling system 110 to be used with the bedding system 140. Third port 200 is attached by conventional means to the surface of middle sheet 160 which faces the top sheet 152.

A fourth port 202 is in fluid communication with fourth distribution chamber 190 to either receive temperature controlled gas from or discharge temperature controlled gas to the heating/cooling system 110 to be used with the bedding system 140. Fourth port 202 is attached by conventional means to the surface of middle sheet 160 which faces the top sheet 152. It will be appreciated that when third port 200 is receiving temperature controlled gas then fourth port 202 will be discharging temperature controlled gas and vice versa.

With further reference to FIGS. 9 and 10 and as previously noted, top sheet 152, drapes 144, 146, 148, and 150, and middle sheet 160 are removably attached together along their side edges by fastening means 192. Where side edges 145 and 149 and also where side edges 147 and 151 are removably attached together, fastening means 192 forms a discontinuous seam or line which is interrupted by passageways 204 between portions of fastening means 192 (see FIG. 10). Passageways 204 permits gas to move or flow from second plurality of separate passageways 186 to the volume 206 between drapes 144 and 148 and to the volume 208 between drapes 146 and 150. Drapes 144, 146, 148, and 150 are also removably attached together along their side edges 210, 212, 214 and 216, respectively, by fastening means 218 such as VELCRO. Apertures 220 are formed in drape 144 and apertures 222 are formed in drape 146 to allow the gas in volumes 206 and 208 to flow through the apertures into the volume enclosed by the drapes and thereby thermally bath the patient with the thermally controlled gas.

It will be appreciated that bedding system 140 will be operatively connected to heating/cooling system 110 in a manner similar to the connection of temperature controlled blanket 10 and the heating/cooling system 110 and the heating/cooling system 110 will be operated in the same manner as previously discussed.

Figure 12:
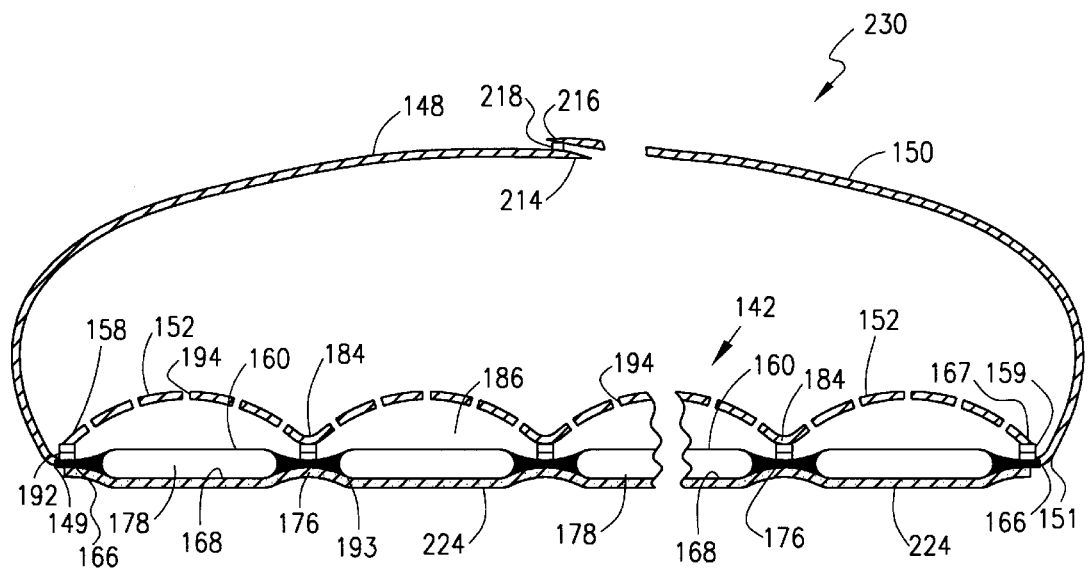
FIG. 12 is an enlarged sectional view similar to that of FIG. 9 showing an additional embodiment of the present invention.

Referring now to FIG. 12, reference numeral 230 generally indicates an additional embodiment of the present inventive bedding system. Bedding system 230 comprises central portion 142 and drapes 148 and 150. It will be appreciated that bedding system 230 includes elements similar to those elements of bedding system 140 but does not include drapes 144 and 146. Bedding system 230 is positioned on a bed and the patient is positioned on the central portion 142 and drapes 144 and 146 are then positioned over the patient to provide a gas envelope around the patient with the gas being provided to the envelop through apertures 194. Bedding system 230 includes sheet 224 which is attached to the surface of bottom sheet 168 by conventional means such as RF bonding, heat bonding, adhesives, etc. Sheet 224 comprises a soft fabric material.

It will be appreciated that heating/cooling system 110 will be connected to and operated with bedding system 230 as it is with bedding system 140.

Figure 13:
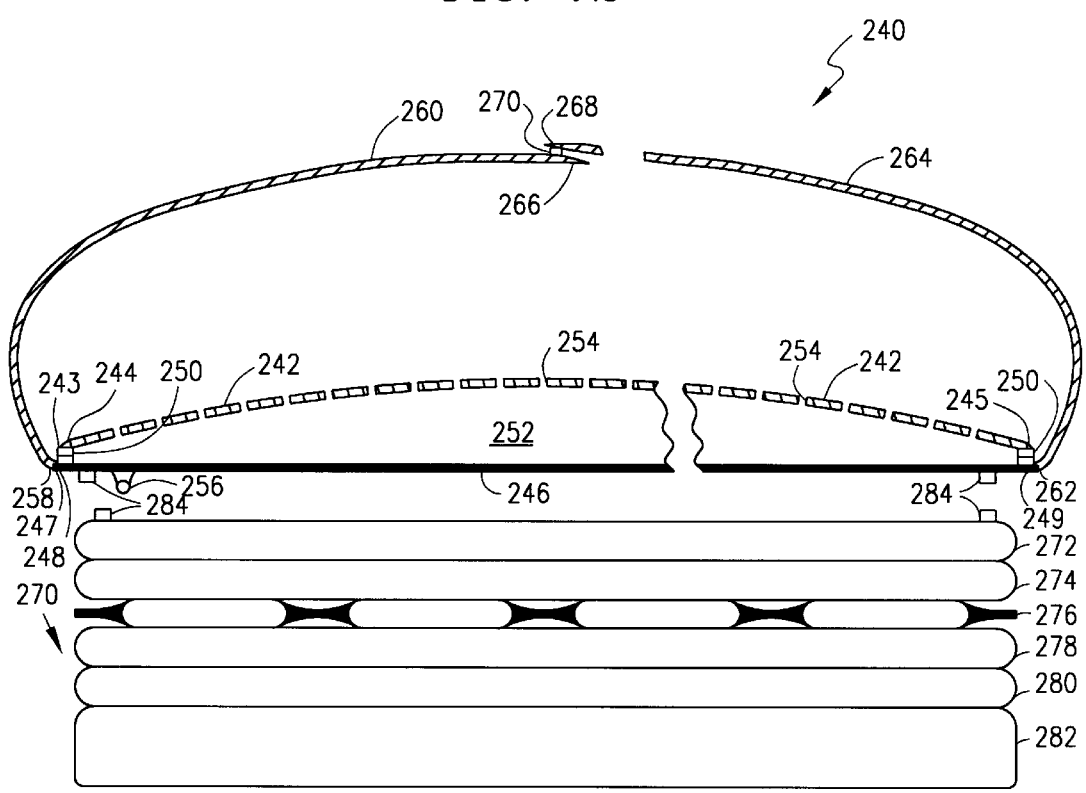
FIG. 13 is an enlarged sectional view similar to that of FIG. 12 showing an additional embodiment of the present invention positioned on a bed which incorporates a temperature controlled fluid recirculating system.

Referring now to FIG. 13, reference numeral 240 generally indicates an additional embodiment of the present inventive bedding system. Bedding system 240 comprises a top sheet 242 having a periphery 243 which includes a first side edge 244 and a second opposing side edge 245 and a bottom sheet 246 having a periphery 247 which includes a first side edge 248 and a second opposing side edge 249. Bottom sheet 246 is formed of a fluid impermeable material which will not let gas therethrough. Top sheet 242 is formed of a flexible material such as a fabric material. In the preferred embodiment, the fabric material comprises linen. Top sheet 242 is removably attached to bottom sheet 246 along their periphery 243 and 247, respectively, by fastening means 250 (such as VELCRO) to form a gas chamber 252. A plurality of apertures 254 are formed in top sheet 242 to allow temperature controlled gas from gas chamber 252 to escape toward and against the person laying on top sheet 242. The number and size of the apertures 254 are commensurate with the specifications of the heating/cooling system 110 which supplies the temperature controlled gas to gas chamber 252. The temperature controlled gas is supplied to gas chamber 252 through port 256. First side edge 258 of drape 260 is removably attached to first side edge 248 of bottom sheet 246 by fastening means 250. First side edge 262 of drape 264 is removably attached to second opposing side edge 249 of bottom sheet 246 by fastening means 250. Second opposing side edge 266 of drape 260 is removably attached to second opposing side edge 268 of drape 264 by fastening means 270 such as VELCRO.

Bedding system 240 is positioned on bed 270 and the patient is positioned on the top sheet 242 and drapes 260 and 264 are then positioned over the patient to provide a gas envelope around the patient with the gas being provided to the gas envelop through apertures 254 in top sheet 242.

It will be appreciated that bedding system 240 may be used with various configurations and designs of beds for patients with bed 270 being a generalized patient bed which provides the fluid portion of the overall bedding system while bedding system 240 provides the gas portion of the overall bedding system. Bed 270 could comprise such layers as a gel layer 272, a fluid layer 274, a water layer 276, an air layer 278, another fluid layer 280, a base section 282, etc. It will be appreciated that the layers may be positioned in any particular sequence and some beds may have only half as many layers as shown here. Bedding system 240 is removably attached to bed 270 by fastening means 284 such as VELCRO.

Figure 14:
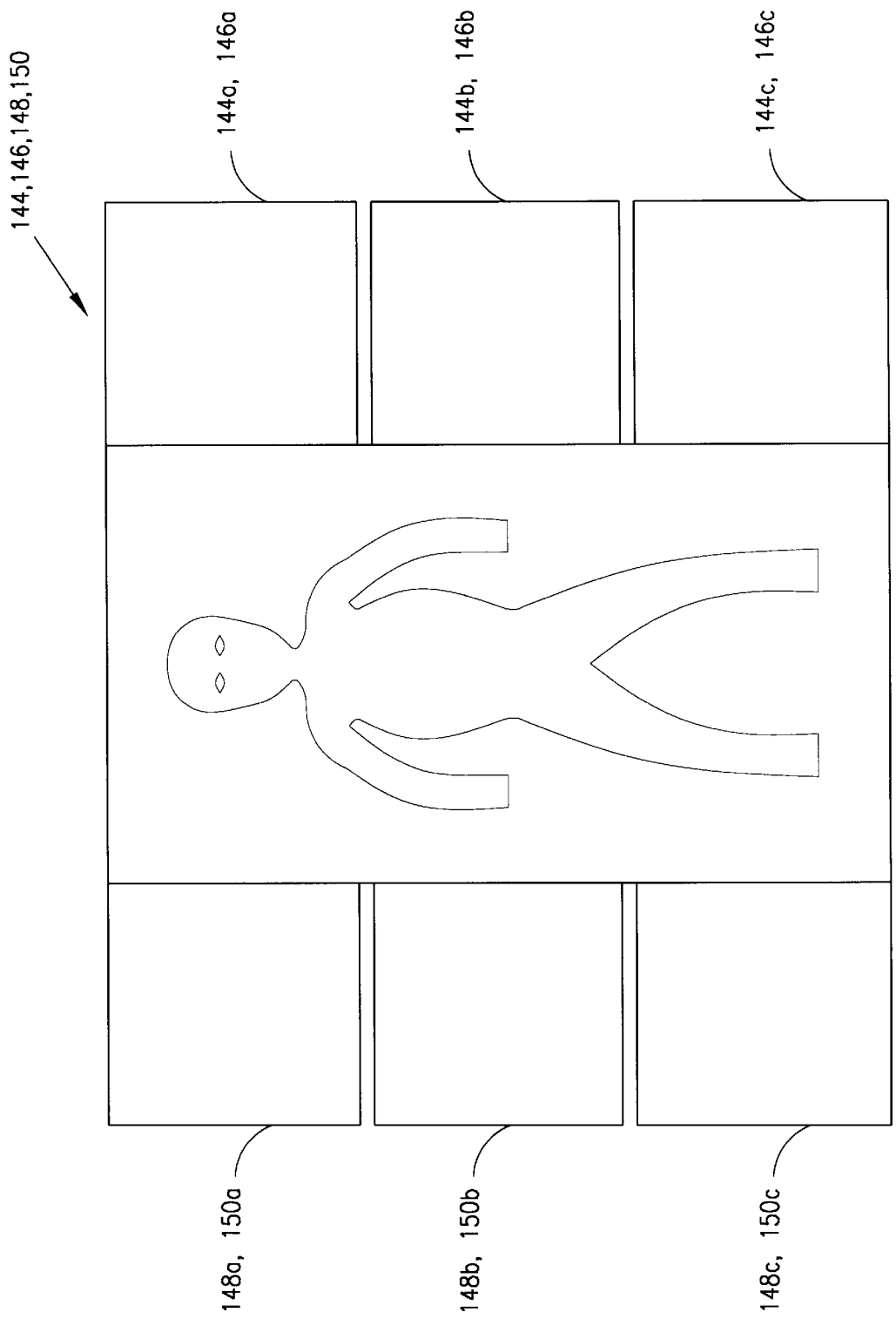
FIG. 14 is an enlarged top plan view showing an additional embodiment of the present invention in use with a patient.

Referring now to FIG. 14, there is shown a top plan view which applies to FIGS. 9, 12 and 13 and shows that drapes 144, 146, 148 or 150 may be divided into two or more sections 144a, 144b, 144c, 146a, 146b, 146c, 148a, 148b, 148c, 150a, 150b or 150c. The division of drapes 144, 146, 148 or 150 into two or more sections allows convenient and easy exposure of a portion of the body of a patient while maintaining coverage of the remaining portion or portions of the body of a patient.

Figure 15:
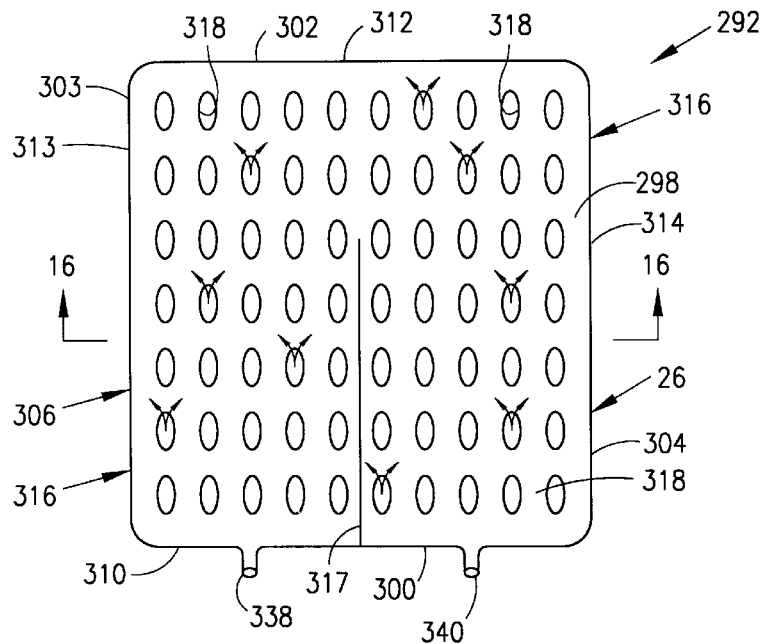
FIG. 15 is a view of the top surface of an additional embodiment of the present invention.
Figure 16:
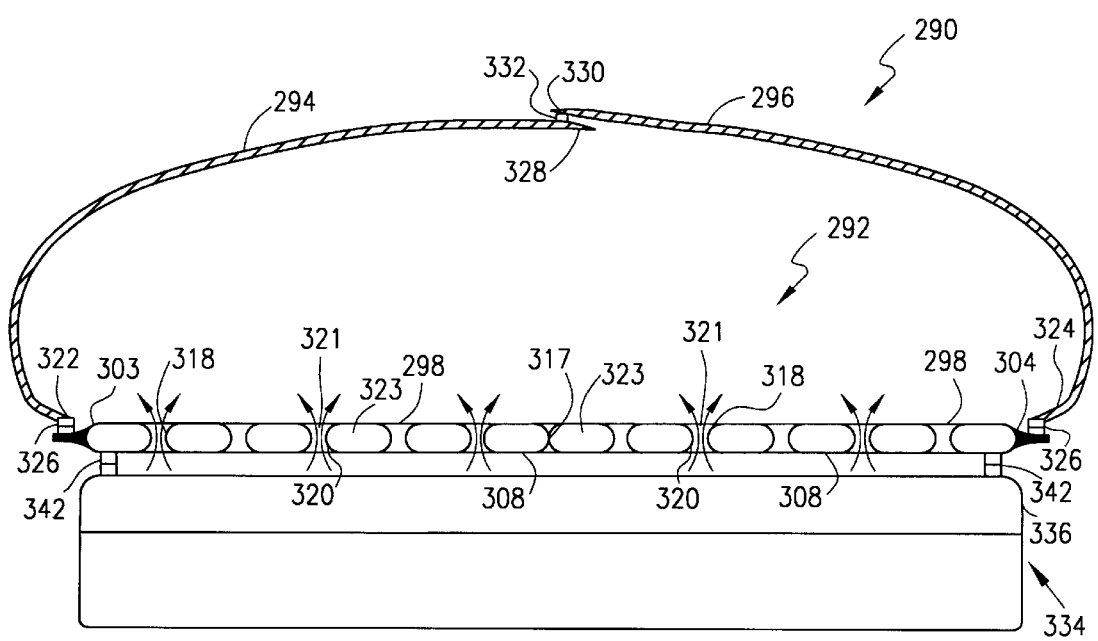
FIG. 16 is an enlarged sectional view of the present invention taken along line 16—16 in FIG. 15.

Referring now to FIGS. 15 and 16, reference numeral 290 generally indicates an additional embodiment of the present inventive bedding system. Bedding system 290 comprises central portion 292 and drapes 294 and 296. Central portion 292 comprises a top sheet 298 having a first end 300, an opposing second end 302, a first side edge 303 and a second opposing side edge 304 to form a periphery 306 and a bottom sheet 308 having a first end 310, an opposing second end 312, a first side edge 313 and a second opposing side edge 314 to form a periphery 316. A plurality of apertures 318 are formed in top sheet 298 and a plurality of apertures 320, of the same size and shape as apertures 318, are formed in bottom sheet 308 with the apertures in the top and bottom sheets being in alignment.

Top sheet 298 and bottom sheet 308 are formed of a fluid impermeable heat bondable plastic such as polyethylene, polyvinylchloride, or other similar material. Top sheet 298 is attached or secured to bottom sheet 308 along their periphery 306 and 316, respectively, along a generally central line 317 and along the periphery of apertures 318 and 320 to form ports 321 thereby forming a space or volume 323 which will hold a temperature controlled liquid for circulation therethrough. The alignment and attachment of the peripheries of apertures 318 and 320 form ports 321 through central portion 292 to allow gas to flow therethrough.

A first port 338 is in fluid communication with space or volume 323 of central portion 292 to either receive temperature controlled liquid, e.g. water, from or discharge temperature controlled liquid to the particular heating/cooling system to be used with the bedding system 290.

A second port 340 is in fluid communication with space or volume 323 of central portion 292 to either receive temperature controlled liquid, e.g. water, from or discharge temperature controlled liquid to the particular heating/cooling system to be used with the bedding system 290.

First side edge 322 of drape 294 is removably attached to first side edge 303 of top sheet 298 and first side edge 324 of drape 296 is removably attached to second opposing side edge 304 of top sheet 298 by fastening means 326 such as VELCRO. Drapes 294 and 296 are also removably attached together along their second opposing side edges 328 and 330, respectively, by fastening means 332 such as VELCRO.

Central portion 292 can be used with or without drapes 294 and 296 and is primarily for use on a patient bed 334 which includes an air mattress 336 which provides a flow of temperature controlled gas or air upwardly through ports 321 and around a patient which is laying on the central portion 292. If used with the drapes, central portion 292 is positioned on the air mattress 336 and the patient is positioned on the top sheet 298 and drapes 294 and 296 (if used) are then positioned over the patient to provide a gas envelope around the patient with the gas or air being provided to the gas envelop from air mattress 336 through ports 321. Central portion 292 provides additional temperature control of the air or gas passing upward from air mattress 336 as well as the air or gas in the gas envelope provided by drapes 294 and 296. Central portion 292 is removably attached to bed 334 by fastening means 342 such as VELCRO.

From the foregoing detailed description, it can be appreciated that the present invention is capable of providing an improved temperature controlled blanket and an improved temperature controlled bedding system by using a liquid fluid with a significantly larger thermal capacity to uniformly heat or cool gaseous fluid delivered to the patient and providing the capability of counter flow or co-flow heat exchanging principles to achieve temperature uniformity across different sections of the temperature controlled blanket. The drapes of the inventive bedding system provide a gas envelope around the person or patient laying on the central portion of the bedding system. In a further embodiment of the bedding system, the air portion of a bedding system is provided for use with a patient bed which supplies the fluid portion of the overall bedding system. In a further embodiment of the bedding system, the fluid portion of a bedding system is provided for use with a patient bed which supplies the air portion of the overall bedding system.

While particular embodiments of the present invention have been described, it will be appreciated by those skilled in the art that various modifications, alternatives, variations, etc., may be made without departing from the spirit and scope of the invention as defined in the appended claims.

What is claimed is:

1. A temperature controlled blanket, said temperature controlled blanket comprising:
    a first sheet of flexible material;
    a second sheet of fluid impermeable flexible material;
    a third sheet of fluid impermeable flexible material;
    said first sheet of flexible material attached to said second sheet of fluid impermeable flexible material to form a gas chamber therebetween;
    said second sheet of fluid impermeable flexible material and said third sheet of fluid impermeable flexible material secured to each other along a first plurality of portions to form at least one U-shaped secondary passage therebetween and to form first and second distribution chambers located at opposite ends of said at least one U-shaped secondary passage and in fluid-communication therewith, an outer surface of said third sheet of fluid impermeable flexible material includes a sheet of insulating material secured thereto;
    a first port in fluid communication with said first distribution chamber;
    a second port in fluid communication with said second distribution chamber;
    a third port in fluid communication with said gas chamber; and
    wherein said first sheet of flexible material has a plurality of apertures in fluid communication with said gas chamber.

2. The temperature controlled blanket as set forth in claim 1 wherein said third sheet of fluid impermeable flexible material comprises plastic.

3. The temperature controlled blanket as set forth in claim 2 wherein said plastic comprises polyvinylchloride.

4. The temperature controlled blanket as set forth in claim 2 wherein said plastic comprises polyethylene.

5. The temperature controlled blanket as set forth in claim 1 wherein said second sheet of fluid impermeable flexible material comprises plastic.

6. The temperature controlled blanket as set forth in claim 5 wherein said plastic comprises polyvinylchloride.

7. The temperature controlled blanket as set forth in claim 5 wherein said plastic comprises polyethylene.

8. The temperature controlled blanket as set forth in claim 1 wherein said first sheet of flexible material comprises fabric material.

9. The temperature controlled blanket as set forth in claim 8 wherein said fabric material comprises linen.

10. The temperature controlled blanket as set forth in claim 1 wherein said insulating material on said outer surface of said third sheet of fluid impermeable flexible material includes a soft fabric material.

11. The temperature controlled blanket as set forth in claim 10 wherein said soft fabric material is RF sealed to said outer surface of said third sheet of fluid impermeable flexible material.

12. The temperature controlled blanket as set forth in claim 1 further including a fourth port in fluid communication with said gas chamber.

13. The temperature controlled blanket as set forth in claim 12 further including a heating/cooling system connected to said third and fourth ports for selectively circulating a temperature controlled gas through said gas chamber.

14. The temperature controlled blanket as set forth in claim 13 wherein said heating/cooling system includes means to control a pressure of the temperature controlled gas to the temperature controlled blanket.

15. A temperature controlled blanket, said temperature controlled blanket comprising:
    a first sheet of flexible material;
    a second sheet of fluid impermeable flexible material;
    a third sheet of fluid impermeable flexible material;
    said first sheet of flexible material attached to said second sheet of fluid impermeable flexible material to form a gas chamber therebetween;
    said second sheet of fluid impermeable flexible material and said third sheet of fluid impermeable flexible material secured to each other along a first plurality of portions to form at least one U-shaped secondary passage therebetween and to form first and second distribution chambers located at opposite ends of said at least one U-shaped secondary passage and in fluid communication therewith;
    a first port in fluid communication was said first distribution chamber;
    a second port in fluid communication with said second distribution chamber;
    a third port in fluid communication with said gas chamber; and
    a heating/cooling system connected to said first and second ports for selectively circulating a temperature controlled liquid through said at least one U-shaped secondary passage between said second sheet of fluid impermeable flexible material and said third sheet of fluid impermeable flexible material; and wherein said first sheet of flexible material has a plurality of apertures in fluid communication with said gas chamber.

16. The temperature controlled blanket as set forth in claim 15 wherein said heating/cooling system includes means to control a pressure of the temperature controlled liquid to the temperature controlled blanket.

17. A temperature controlled blanket, said temperature controlled blanket comprising:

a first sheet of flexible material;

a second sheet of fluid impermeable flexible material, said first sheet of flexible material is removably attached to said second sheet of fluid impermeable flexible material to form said gas chamber therebetween;

a third sheet of fluid impermeable flexible material;

said second sheet of fluid impermeable flexible material and said third sheet of fluid impermeable flexible material secured to each other along a first plurality of portions to form at least one U-shaped secondary passage therebetween and to form first and second distribution chambers located at opposite ends of said at least one U-shaped secondary passage and in fluid communication therewith;

a first port in fluid communication was said first distribution chamber;

a second port in fluid communication with said second distribution chamber;

a third port in fluid communication with said gas chamber; and wherein said first sheet of flexible material has a plurality of apertures in fluid communication with said gas chamber.

18. A temperature controlled blanket, said temperature controlled blanket comprising:

a first sheet of flexible material;

a second sheet of fluid impermeable flexible material;

a third sheet of fluid impermeable flexible material;

said first sheet of flexible material attached to said second sheet of fluid impermeable flexible material to form a gas chamber therebetween;

said second sheet of fluid impermeable flexible material and said third sheet of fluid impermeable flexible material secured to each other along a first plurality of portions to form at least one U-shaped secondary passage therebetween and to form first and second distribution chambers located at opposite ends of said at least one U-shaped secondary passage and in fluid communication therewith;

a first port in fluid communication was said first distribution chamber;

a second port in fluid communication with said second distribution chamber;

a third port in fluid communication with said gas chamber; and wherein said first sheet of flexible material has a plurality of apertures in fluid communication with said gas chamber;

said first sheet of flexible material is attached to said second sheet of fluid impermeable flexible material such that said gas chamber comprises at least one primary passage, a third distribution chamber, and a fourth distribution chamber therebetween;

said third and fourth distribution chambers being in fluid communication with opposite ends of at least one primary passage, wherein said third port is in fluid communication with said gas chamber with said third distribution chamber; and wherein said plurality of apertures of said first sheet of flexible material are in fluid communication with said at least one primary passage.

19. The temperature controlled blanket as set forth in claim 18 wherein said at least one U-shaped secondary passage extends from said first distribution chamber to said second distribution chamber.

20. The temperature controlled blanket as set forth in claim 18 wherein said at least one primary passage is formed in the shape of a U from said third distribution chamber to said fourth distribution chamber.

21. The temperature controlled blanket as set forth in claim 18 wherein said third sheet of fluid impermeable flexible material comprises plastic.

22. The temperature controlled blanket as set forth in claim 21 wherein said plastic comprises polyvinylchloride.

23. The temperature controlled blanket as set forth in claim 21 wherein said plastic comprises polyethylene.

24. The temperature controlled blanket as set forth in claim 18 wherein said second sheet of fluid impermeable flexible material comprises plastic.

25. The temperature controlled blanket as set forth in claim 24 wherein said plastic comprises polyvinylchloride.

26. The temperature controlled blanket as set forth in claim 24 wherein said plastic comprises polyethylene.

27. The temperature controlled blanket as set forth in claim 18 wherein said first sheet of flexible material comprises fabric material.

28. The temperature controlled blanket as set forth in claim 27 wherein said fabric material comprises linen.

29. The temperature controlled blanket as set forth in claim 18 wherein an outer surface of said third sheet of fluid impermeable flexible material which is farthest from said second sheet of fluid impermeable flexible material includes a soft fabric material secured thereto.

30. The temperature controlled blanket as set forth in claim 29 wherein said soft fabric material is RF sealed to said outer surface of said third sheet of fluid impermeable flexible material.

31. The temperature controlled blanket as set forth in claim 18 wherein an outer surface of said third sheet of fluid impermeable flexible material which is farthest from said second sheet of fluid impermeable flexible material includes a sheet of insulating material secured thereto.

32. The temperature controlled blanket as set forth in claim 18 further including a heating/cooling system connected to said first and second ports for selectively circulating a temperature controlled liquid through said at least one U-shaped second passage between said second sheet of fluid impermeable flexible material and said third sheet of fluid impermeable flexible material.

33. The temperature controlled blanket as set forth in claim 32 wherein said heating/cooling system includes means to control a pressure of the temperature controlled liquid to the temperature controlled blanket.

34. The temperature controlled blanket as set forth in claim 18 further including a fourth port in fluid communication with said gas chamber with said fourth distribution chamber.

35. The temperature controlled blanket as set forth in claim 34 further including a heating/cooling system connected to said third and fourth ports for selectively circulating a temperature controlled gas through said at least one primary passage between said first sheet of flexible material and said second sheet of fluid impermeable flexible material.

36. The temperature controlled blanket as set forth in claim 35 wherein said heating/cooling system includes means to control a pressure of the temperature controlled gas to the temperature controlled blanket.

37. The temperature controlled blanket as set forth in claim 18, wherein:
said first sheet of flexible material is removably attached to said second sheet of fluid impermeable flexible material to form said gas chamber therebetween; and
said first sheet of flexible material is removably attached to said second sheet of fluid impermeable flexible material to form said at least one primary passage therebetween.

38. The temperature controlled blanket as set forth in claim 18 wherein said at least one U-shaped secondary passage is aligned with said at least one primary passage.

39. The temperature controlled blanket as set forth in claim 18 wherein said at least one primary passage comprises a plurality of primary passages.

40. The temperature controlled blanket as set forth in claim 39 wherein said plurality of primary passages are parallel to one another.

* * * * *